US00PP13813P29

(12) United States Plant Patent
Jones

(10) Patent No.: US PP13,813 P2
(45) Date of Patent: May 13, 2003

(54) PELARGONIUM PLANT NAMED 'SARAH DON'

(76) Inventor: Roger Jones, Oakleigh Nurseries Petersfield Road, Monkwood Alresford Hampshire SO24 OHB (GB)

( * ) Notice: Subject to any disclaimer, the term of this patent is extended or adjusted under 35 U.S.C. 154(b) by 0 days.

(21) Appl. No.: 10/002,426

(22) Filed: Nov. 21, 2001

(51) Int. Cl.[7] ..... A01H 5/00

(52) U.S. Cl. ..... Plt./331

(58) Field of Search ..... Plt./331

*Primary Examiner*—Kent Bell

(57) ABSTRACT

A new cultivar of Pelargonium plant named 'Sarah Don' that is characterized by a dense mounding habit, golden-yellow and lime-green variegated foliage, and mauve flowers with dark purple-pink markings. In combination these traits set 'Sarah Don' apart from all other existing varieties of Pelargonium known to the inventor.

2 Drawing Sheets

Genus: Pelargonium.
Species: *domesticum.*
Denomination: 'SARAH DON'.

BACKGROUND OF THE INVENTION

The present invention relates to a new and distinct cultivar of geranium that is grown as an ornamental for its golden-yellow and lime-green variegated foliage. The new cultivar is known botanically as *Pelargonium×domesticum* and will be referred to hereinafter by the cultivar name 'Sarah Don'.

'Sarah Don' is a naturally occurring branch sport that was discovered by the inventor at the base of a commercially grown Pelargonium 'Darmsden' (unpatented) in a cultivated area of Hampshire, England. On Nov. 12, 1998 the inventor selected 'Sarah Don' for its unique golden-yellow and lime-green variegated foliage. 'Sarah Don' is distinguishable from the parent plant by its leaf color and variegation. The parent Pelargonium 'Darmsden' does not exhibit any variegation.

'Sarah Don' is from a group of Pelargonium commonly referred to as Angel Pelargonium. Within this group the flowers are smaller and more numerous than in any other group of Pelargonium.

'Sarah Don' was first asexually propagated by the inventor in 1998 in a cultivated area of Hampshire, England. The method used for asexual propagation was vegetative cuttings. Since that time the characteristics of the new cultivar have been determined stable and are reproduced true to type in successive generations.

SUMMARY OF THE INVENTION

The following traits have been repeatedly observed and represent the distinguishing characteristics of the new cultivar 'Sarah Don'. In combination these traits set 'Sarah Don' apart from all other Pelargonium known to the inventor. 'Sarah Don' has not been tested under all possible conditions and phenotypic differences may be observed with variations in environmental, climatic and cultural conditions, however, without any variance in genotype.

1. Pelargonium 'Sarah Don' exhibits golden-yellow and lime-green variegated foliage.
2. Pelargonium 'Sarah Don' flowers profusely and exhibits mauve flowers with dark purple-pink markings.

3. Pelargonium 'Sarah Don' grows to 60 cm. in height and 80 cm. in width at maturity.
4. Pelargonium 'Sarah Don' exhibits a dense, naturally determining, mounding habit.
5. Pelargonium 'Sarah Don' is hardy to USDA Zone 8.

BRIEF DESCRIPTION OF THE DRAWINGS

The accompanying drawings illustrate the overall appearance of the new cultivar 'Sarah Don' showing the colors as true as it is reasonably possible to obtain in colored reproductions of this type. The plants in the photographs were grown in Arroyo Grande, Calif. in one-litre containers. The plants were 12-months-old at the time and grown in a greenhouse. They were photographed in July.

Sheet 1 illustrates an entire plant from a side perspective. Sheet 2 shows a close-up view of the flowers and the foliage. All photographs were made using conventional techniques and although colors may appear different from the color values cited in the detailed botanical description, due to light reflectance, they are as accurate as possible by conventional photography. The detailed botanical description accurately describes the actual colors of the new cultivar 'Sarah Don'.

BOTANICAL DESCRIPTION OF THE PLANT

The following is a detailed description of the new Pelargonium named 'Sarah Don'. Information was collected in Arroyo Grande Calif. from 12-month-old plants grown in a greenhouse in one-litre containers. The color determinations are in accordance with The R.H.S. Colour Chart of The Royal Horticultural Society, London, England, except where general color terms of ordinary dictionary significance are used. The growing requirements are similar to other Pelargonium.

Botanical classification: *Pelargonuim×domesticum* 'Sarah Don'.
Species: *Domesticum.*
Commercial classification: Perennial.
Common name: Regal pelargonium; Angel type.
Use: Ornamental for container or perennial border.
Cultural requirements: Plant in full sun or partial shade and fast-draining soil.

Parentage: Pelargonium 'Sarah Don' is a branch sport of Pelargonium 'Darmsden'. The parent plant is Pelargonium 'Darmsden'.

Plant description:

*Bloom period.*—Spring and summer, extending into fall.

*Plant habit.*—Erect, dense and mounding.

*Height.*—30 cm. in height in a 1-litre container.

*Width.*—30 cm. in width in a 1-litre container.

*Hardiness.*—USDA Zone 8.

*Propagation.*—Propagation is accomplished using vegetative cuttings.

*Time to develop roots.*—10 to 14 days, when rooted on a heated bench.

*Crop time.*—Eight weeks are needed to produce a 10-centimeter container from a rooted cutting and two additional months are needed to produce a 1-litre container.

*Disease problems.*—Using contaminated compost can lead to blackleg and Pelargonium collapse.

Stem:

*Shape.*—Cylindrical.

*Stem color.*—144B.

*Stem dimensions.*—30 cm. in length and 0.75 cm. in diameter.

*Stem surface.*—Pubescent with whitish hairs up to 3 mm. in length.

*Basal stem shape.*—Columnar.

*Basal stem color.*—146A.

*Branching.*—Basal branching. Branching from all nodes once flowering is initiated.

*Internode length.*—1.25–3 cm. between nodes.

*Branching habit.*—Basal branching with erect stems.

Foliage:

*Type.*—Evergreen.

*Shape.*—Reniform to trilobed leaves.

*Division.*—Simple.

*Apex.*—Rounded.

*Base.*—Leaves with cordate bases and leaves with truncate bases are both individually present on each individual plant.

*Venation.*—Palmate with veins depressed on adaxial surface and protruding on abaxial surface.

*Vein color* (*adaxial surfaces*).—147A.

*Vein color* (*abaxial surfaces*).—147C.

*Margins.*—Undulate and biserrate.

*Texture.*—Flexible.

*Arrangement.*—Alternate and spiral.

*Attachment.*—Petiolate.

*Surfaces* (*adaxial and abaxial*).—Pubescent.

*Mature leaf dimensions.*—Mature leaf dimensions range from 2–3 cm. in length and 3–4.25 cm. in width.

*Young leaf dimensions.*—1.25 cm. in length and 1.75 cm. in width.

*Leaf color* (*adaxial surface*).—Both colors 143A and 11C are individually present on each individual leaf. 143A is the color of the center and 11C is the margin color.

*Leaf color* (*abaxial surface*).—Both colors 147C and 11A are individually present on each individual leaf. 147C is the color of the center and 11A is the margin color.

*Petiole shape.*—Sulcate.

*Petiole color.*—144A.

*Petiole surface.*—Pubescent.

*Color of pubescence.*—156D.

*Petiole dimensions.*—2 cm. in length and 1 mm. in diameter. Petiole can extend up to 12 cm. under low light conditions.

*Stipules.*—Present and distinctive.

*Stipule dimensions.*—5 mm. in length and 3 mm. in width.

*Color of stipules.*—145A.

*Surface of stipules.*—Pubescent.

*Stipule apex.*—Acuminate.

*Stipule base.*—Truncate.

*Stipule margin.*—Entire.

*Number of stipules.*—2 stipules at the base of each petiole.

Flowers:

*Inflorescence.*—Umbel.

*Dimensions of inflorescence.*—6 cm. in diameter and 3 cm. in depth.

*Flower shape.*—Funnelform.

*Flower dimensions.*—3 cm. in width and 3 cm. in length.

*Number of flowers per umbel.*—1–4 flowers per umbel.

*Lastingness of flower.*—Most of the time an individual flower lasts 7–10 days, and in cool dry conditions flowers last longer than 10 days.

*Persistent or self-cleaning.*—Self-cleaning.

*Aspect.*—Facing upward.

*Sexuality.*—Bisexual.

*Bud dimensions.*—0.50 cm. in width and 1 cm. in length.

*Bud shape.*—Oval.

*Bud color.*—Both colors 144A and 72A are individually present on buds that have begun opening. Buds that are completely closed are the color 144A. Both of these buds are present on an individual plant.

*Flower color* (*adaxial surfaces*).—Pale color of lower petals is 76C, dark upper petals are 74A, darkest spots on petals are 79A, and dark veining on petals is 72A.

*Flower color* (*abaxial surfaces*).—Pale color of lower petals is 76C, dark upper Petals are 74A, darkest spots on petals are 79A, and dark veining on petals is 72A.

*Petals.*—Five in number (2 upper and 3 lower).

*Petal shape.*—Closest to obovate but exhibiting a narrower base.

*Petal apex.*—Rounded.

*Petal base.*—Attenuate.

*Fused or unfused.*—Unfused.

*Petal dimensions.*—Lower pale colored petals are 3 cm. in length and 1 cm. in width, and upper dark colored petals are 3 cm. in length and 1.50 cm. in width.

*Petal margin.*—Entire.

*Petal surface.*—Glabrous.

*Calyx dimensions.*—1 cm. in length and 1 cm. in diameter.

*Calyx surface.*—Pubescent.

*Sepals.*—Five in number.

*Sepals fused or unfused.*—Unfused. Some confusion arises from the drawings. Although the sepals appear fused around the bud at the right edge center of Sheet 2, and basally fused on the sepal at the left edge center of Sheet 2, the sepals on the actual plant are unfused but overlapping one another which makes them appear fused in the drawing.

*Sepal dimensions.*—1 cm. in length and 3 mm. in width.

*Sepal margin.*—Entire.
*Sepal color* (*adaxial surface*).—Individual colors 138B and 158D are both present on each individual sepal.
*Sepal color* (*abaxial surface*).—Individual colors 138B and 158D are both present on each individual sepal.
*Sepal surface.*—Pubescent.
*Sepal apex.*—Apiculate.
*Peduncle dimensions.*—3.5 cm. in length and 2 mm. in width.
*Pedicel dimensions.*—1 cm. in length and 1 mm. in diameter.
*Peduncle color.*—138B.
*Pedicel color.*—184A.
*Peduncle surface.*—Pubescent.
*Pedicel surface.*—Pubescent.
*Flower fragrance.*—Flowers have no fragrance.

Reproductive organs:
*Stamens.*—Seven in number.
*Stamen color.*—74D.
*Stamen dimensions.*—1.50 cm. in length and 0.50 mm. in diameter.
*Anther dimensions.*—1.50 mm. in length and .25 mm. in width.
*Anther color.*—77A.
*Anther shape.*—Linear.
*Pollen.*—Present.
*Amount of pollen.*—Moderate amount.
*Color of pollen.*—162A.
*Pistil.*—One.
*Pistil dimensions.*—9 mm. in length and 0.50 mm. in width.
*Pistil color.*—72A.
*Ovary position.*—Superior.
*Ovary color.*—138D.
*Ovary shape.*—Oval.
*Ovary dimensions.*—3 mm. in length and 2 mm. in diameter.

Seed production: Seed production has not been observed to date.

I claim:

1. A new and distinct cultivar of Pelargonium plant named 'Sara Don' as described and illustrated herein.

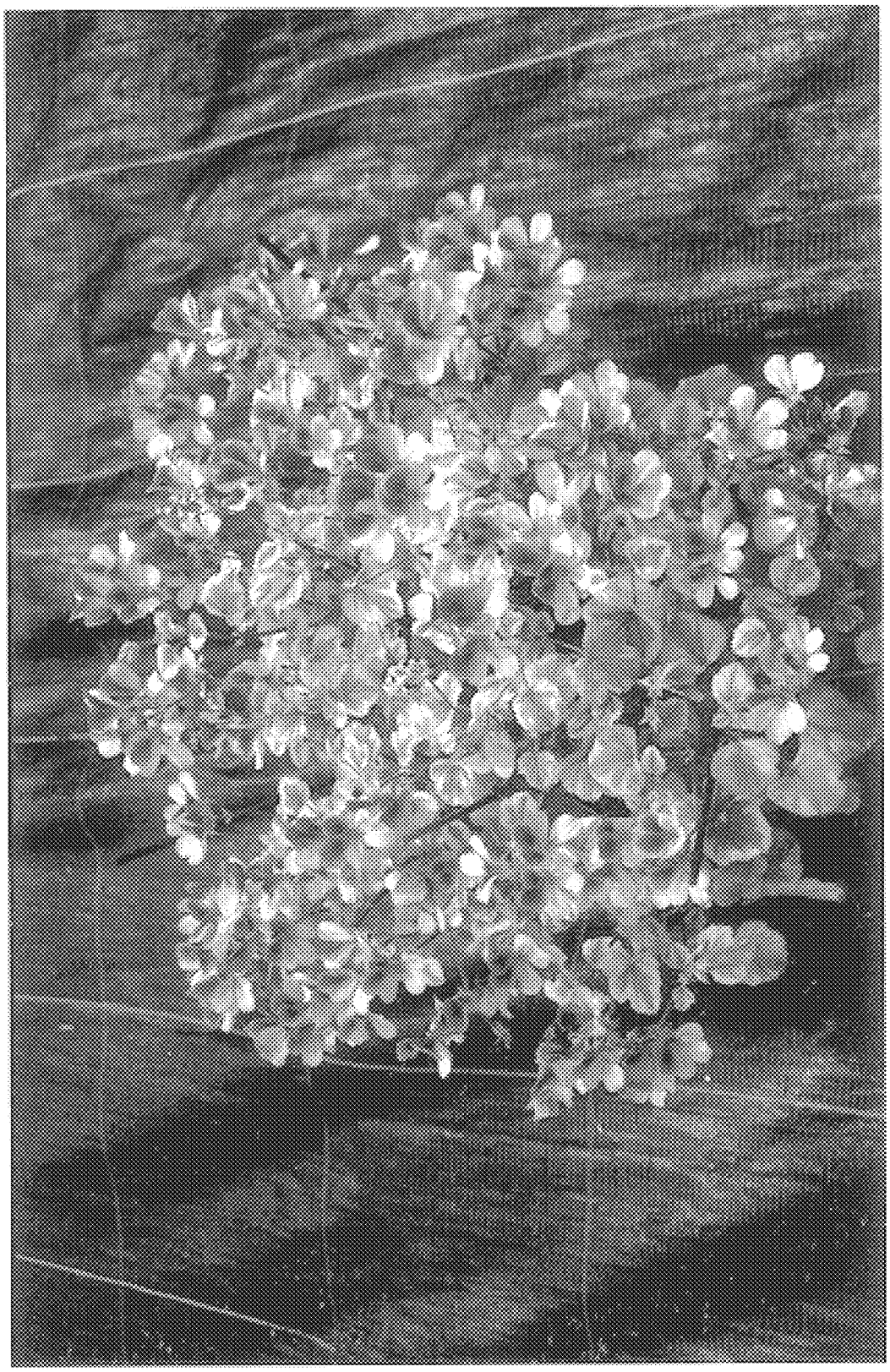

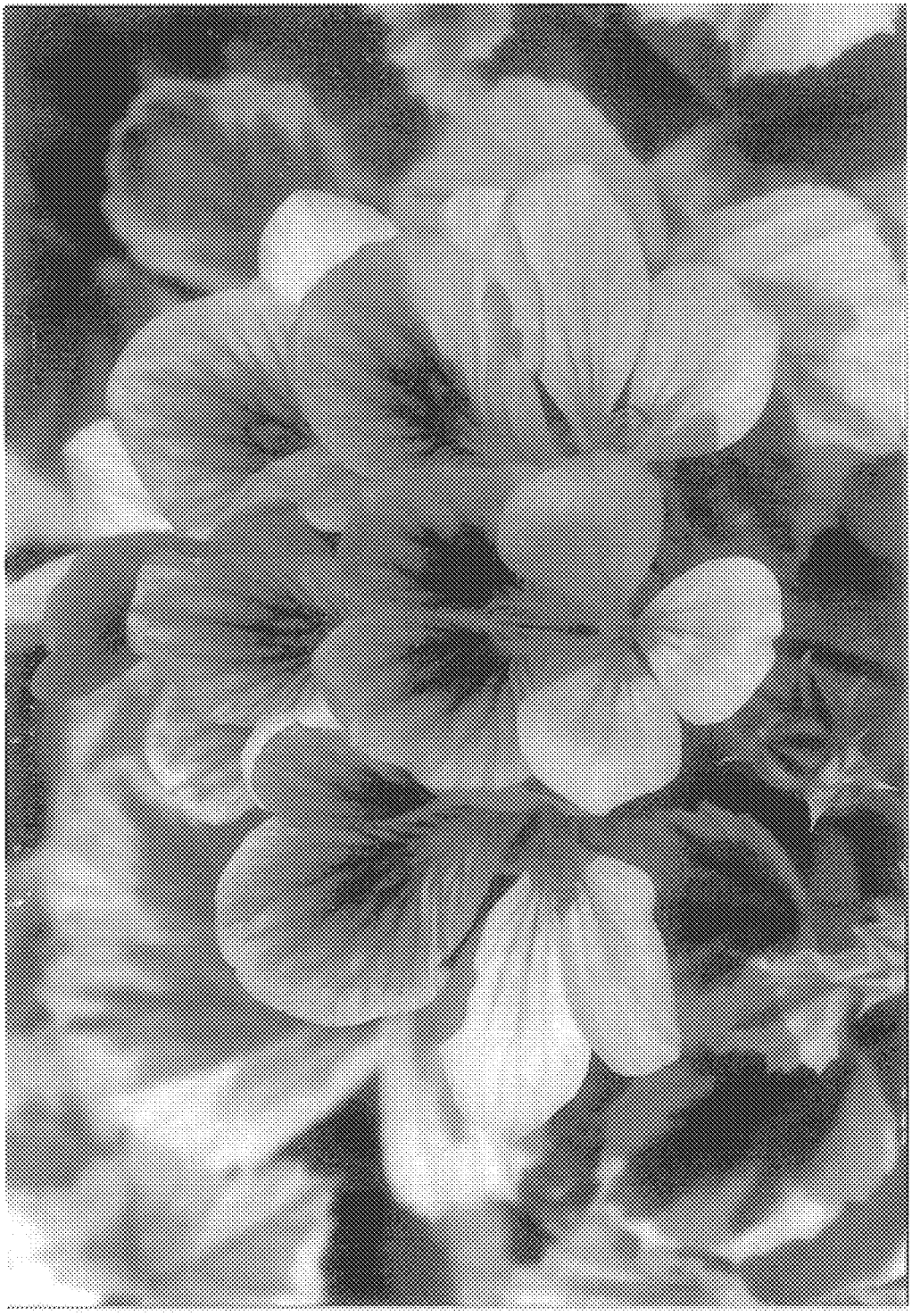

* * * * *